(12) United States Patent  
Fuchss et al.

(10) Patent No.: US 8,546,613 B2  
(45) Date of Patent: Oct. 1, 2013

(54) SGK1 INHIBITORS FOR THE PROPHYLAXIS AND/OR THERAPY OF VIRAL DISEASES AND/OR CARCINOMAS

(75) Inventors: Thomas Fuchss, Bensheim-Auerbach (DE); Rolf Gericke, Seeheim-Jugenheim (DE); Norbert Beier, Reinheim (DE); Florian Lang, Tuebingen (DE); Phillipp Lang, Tuebingen (DE); Karl Lang, Tuebingen (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/867,963

(22) PCT Filed: Feb. 17, 2009

(86) PCT No.: PCT/EP2009/001099  
§ 371 (c)(1),  
(2), (4) Date: Nov. 22, 2010

(87) PCT Pub. No.: WO2009/103484  
PCT Pub. Date: Aug. 27, 2009

(65) Prior Publication Data  
US 2011/0060050 A1   Mar. 10, 2011

(30) Foreign Application Priority Data  
Feb. 18, 2008 (DE) .......................... 10 2008 010 361

(51) Int. Cl.  
*C07C 243/28* (2006.01)  
*A61K 31/16* (2006.01)

(52) U.S. Cl.  
USPC .......................................... 564/150; 514/615

(58) Field of Classification Search  
USPC .......................................... 564/150; 514/615  
See application file for complete search history.

(56) References Cited

U.S. PATENT DOCUMENTS  
7,776,920 B2 * 8/2010 Gericke et al. ................ 514/615

FOREIGN PATENT DOCUMENTS

| WO | 9617840 A1 | 6/1996 |
|---|---|---|
| WO | 2005037773 A1 | 4/2005 |
| WO | 2007093264 A | 8/2007 |
| WO | PCT0901099 R | 7/2009 |

OTHER PUBLICATIONS

Carter et al., Chemotherapy of Cancer, second edition, John Wiley & Sons, N.Y., N.Y., 1981, pp. 362-365.*

* cited by examiner

*Primary Examiner* — Shailendra Kumar  
(74) *Attorney, Agent, or Firm* — Millen, White, Zelano & Branigan, P.C.

(57) ABSTRACT

The present invention relates to a compound of formulas I, Ia, Ib and II,

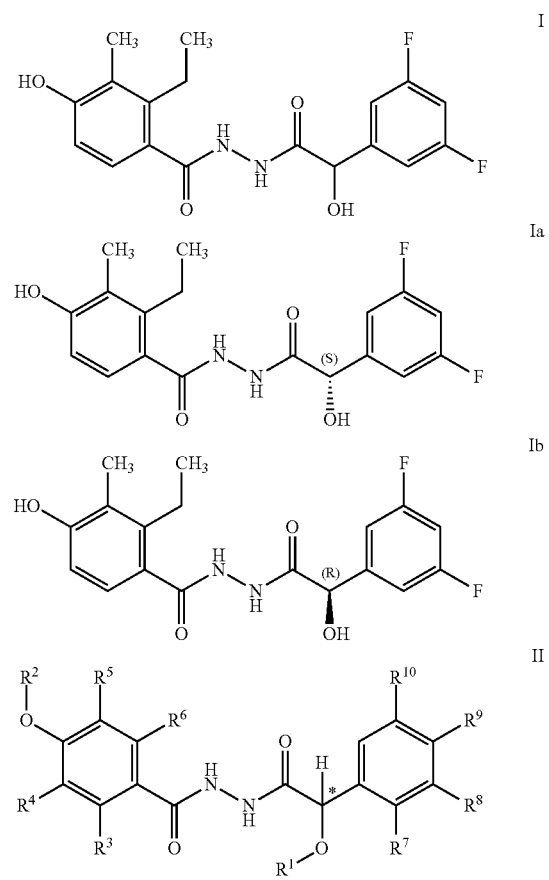

wherein R1 to R11 are herein defined.

6 Claims, 8 Drawing Sheets

SGK1 INHIBITORS FOR THE PROPHYLAXIS AND/OR THERAPY OF VIRAL DISEASES AND/OR CARCINOMAS

This application is a 371 of PCT/EP2009/001099, filed Feb. 17, 2009.

The present invention relates to compounds which inhibit SGK1 (serum and glucocorticoid dependent kinase 1) for the therapeutic treatment of viral diseases and/or carcinomas.

Serum and glucocorticoid dependent kinase 1 (SGK1) is a protein which occurs ubiquitously in eukaryotic cells. SGK1 is under the control of cellular stress, such as, for example, cell shrinkage, and hormones, such as, for example, gluco- and mineralocorticoids. SGK1 is activated by insulin and growth factors via phosphatidylinositol 3-kinase and PDK1 (3-phosphoinositide dependent kinase 1).

SGK1 was originally cloned from rat mammacarcinoma cells (Webster M K, Goya L, Firestone G L. J. Biol. Chem. 268 (16): 11482-11485, 1993; Webster M K, Goya L, Ge Y, Maiyar A C, Firestone G L. Mol. Cell. Biol. 13 (4): 2031-2040, 1993). The human kinase hSGK was cloned as cell volume-regulated gene from liver cells (Waldegger S, Barth P, Raber G, Lang F. Proc. Natl. Acad. Sci. USA 94: 4440-4445, 1997). It has been shown that the rat kinase (Chen S Y, Bhargava A, Mastroberardino L, Meijer O C, Wang J, Buse P, Firestone G L, Verrey F, Pearce D. Proc. Natl. Acad. Sci. USA 96: 2514-2519, 1999; Naray-Fejes-Toth A, Canessa C, Cleaveland E S, Aldrich G, Fejes-Toth G. J. Biol. Chem. 274: 16973-16978, 1999) stimulates the epithelial $Na^+$ channel (ENaC). It has furthermore been shown that increased activity of the ENaC is accompanied by hypertonia (Warnock D G. Kidney Ind. 53 (1): 1824, 1998).

hSGK is also expressed in the brain (Waldegger S, Barth P, Raber G, Lang F. Proc. Natl. Acad. Sci. USA 94: 4440-4445, 1997), where it regulates the voltage-dependent $K^+$ channels Kv1.3. It has been shown that these $K^+$ channels of the Kv1.3 type are involved in regulation of neuronal excitability (Pongs O. Physiol. Rev. 72: 69-88, 1992), regulation of cell proliferation (Cahalan M D and Chandy K G. Cur. Opin. Biotech. 8 (6): 749-756, 1997) and regulation of apoptotic cell death (Szabo I, Gulbin E, Apfel H, Zhan X, Barth P, Busch A E, Schlottmann K, Pongs O, Lang F. J. Biol. Chem. 271: 20465-20469, 1999; Lang F, Szabo I, Lepple-Wienhues A, Siemen D, Gulbins E. News Physiol. Sci. 14: 194-200, 1999). Kv1.3 is furthermore important in regulation of lymphocyte proliferation and function (Cahalan M D and Chandy K G, Cur. Opin. Biotech. 8 (6): 749-756, 1997). Two further members of the SGK family, SGK2 and SGK3, have been cloned (Kobayashi T, Deak M, Morrice N, Cohen P. Biochem. J. 344: 189-197, 1999). It has furthermore been shown that SGKs form a serine/threonine-protein kinase family, which can be regulated transcriptionally and post-transcriptionally. Like SGK1, SGK2 and SGK3 are also activated by, for example, insulin and IGF1 via the PI3 kinase pathway. However, the SGK protein family has to date not been characterised fully.

In the meantime, SGK1 is also known as a target for diverse therapeutic and diagnostic applications.

For example, DE 197 08 173 has shown that hSGK1 has significant diagnostic potential for many diseases which are influenced pathophysiologically by a change in cell volume, such as, for example, hypernatremia, hyponatremia, diabetes mellitus, renal insufficiency, hypercatabolism, hepatic encephalopathy and microbial or viral infections.

DE 199 17 990 has described kinase inhibitors, such as, for example, staurosporin, chelerythrin or transdominantly inhibitory kinase, which can be employed in the therapy of cell volume-dependent diseases.

In addition, WO 2004/079003 A1 discloses the use of SGK1 as diagnostic and therapeutic target for coagulopathies, angiopathies, pulmonary hypertonia and arteriosclerosis.

By contrast, the role of SGK1 in the formation of tumours has been the subject of very controversial and contradictory discussion in the specialist literature.

The invention now has the object of providing further novel therapeutic and diagnostic areas of application using SGK1 as target molecule (target).

The invention also relates to the optically active forms (stereoisomers), the enantiomers, the racemates, the diastereomers and the hydrates and solvates of the compounds of the formulae I, Ia, Ib and II. Solvates of the compounds are taken to mean adductions of inert solvent molecules onto the compounds which form owing to their mutual attractive force. Solvates are, for example, mono- or dihydrates or alcoholates.

The invention relates to a compound of the formula I and its enantiomers of the formula Ia (S configuration) and formula Ib (R configuration):

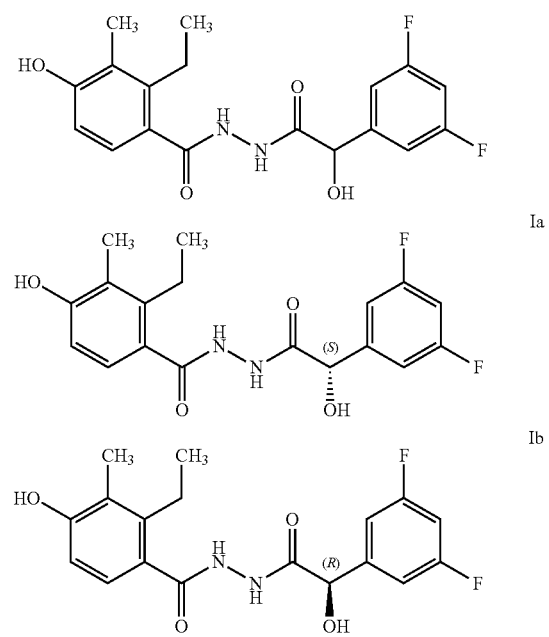

and its pharmaceutically usable tautomers, salts, stereoisomers and the enantiomers, including mixtures thereof in all ratios.

The compound depicted in formula I is N'-[2-(3,5-difluorophenyl)-2-hydroxyacetyl]-2-ethyl-4-hydroxy-3-methyl-benzohydrazide. This compound is preferably used as medicament. The compound depicted by formula I is particularly preferably employed for the prophylaxis and/or treatment of viral hepatitis. This is because, surprisingly, it has been found that the compound of the formula I is an inhibitor of SGK1. Furthermore, it has successfully been shown that said compound is suitable for the therapy of viral diseases and carcinomatous diseases. The preparation of the compound of the formula I is described in greater detail below.

The invention also relates to compounds of the formula II

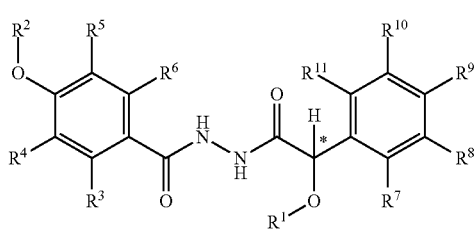

in which
R¹, R² each, independently of one another, denote H, CHO or acetyl,
R³, R⁴, R⁵, R⁶, R⁷,
R⁸, R⁹, R¹⁰, R¹¹ each, independently of one another, denote H, A, OSO₂A, Hal, NO₂, OR¹², N(R¹²)₂, CN, O—COA, —[C(R¹²)₂]ₙCOOR¹², O—[C(R¹²)₂]₀COOR¹², SO₃H, —[C(R¹²)₂]ₙAr, —CO—Ar, O—[C(R¹²)₂]ₙAr, —[C(R¹²)₂]ₙHet, —[C(R¹²)₂]ₙC≡CH, —O—[C(R¹²)₂]ₙC≡CH, —[C(R¹²)₂]ₙCON(R¹²)₂, —[C(R¹²)₂]ₙCONR¹²N(R¹²)₂, O—[C(R¹²)₂]ₙCON(R¹²)₂, O—[C(R¹²)₂]₀CONR¹²N(R¹²)₂, NR¹²COA, NR¹²CON(R¹²)₂, NR¹²SO₂A, N(SO₂A)₂, COR¹², S(O)ₘAr, SO₂NR¹² or S(O)ₘA,
R³ and R⁴ together also denote CH=CH—CH=CH,
R³ and R⁴, R⁷ and R⁸
or R⁸ and R⁹ together also denote alkylene having 3, 4 or 5 C atoms,
in which one or two CH₂ groups may be replaced by oxygen,
A denotes unbranched or branched alkyl having 1-6 C atoms,
in which 1-7H atoms may be replaced by F,
or cyclic alkyl having 3-7 C atoms,
Ar denotes phenyl, naphthyl or biphenyl, each of which is unsubstituted or mono-, di- or trisubstituted by Hal, A, OR¹², N(R¹²)₂, NO₂, CN, phenyl, CON(R¹²)₂, NR¹²COA, NR¹²CON(R¹²)₂, NR¹²SO₂A, COR¹², SO₂N(R¹²)₂, S(O)ₘA, —[C(R¹²)₂]ₙ—COOR¹² and/or —O[C(R¹²)₂]₀COOR¹²,
Het denotes a mono- or bicyclic saturated, unsaturated or aromatic heterocycle having 1 to 4 N, O and/or S atoms, which may be mono-, di- or trisubstituted by Hal, A, OR¹², N(R¹²)₂, NO₂, CN, COOR¹², CON(R¹²)₂, NR¹²COA, NR¹²SO₂A, COR¹², SO₂NR¹², S(O)ₘA, =S, =NR¹² and/or =O (carbonyl oxygen),
R¹² denotes H or A,
Hal denotes F, Cl, Br or I,
m denotes 0, 1 or 2,
n denotes 0, 1, 2 or 3,
o denotes 1, 2 or 3,
for the prophylaxis and/or treatment of viral diseases and/or carcinomas, and their pharmaceutically usable tautomers, salts, stereoisomers and the enantiomers, including mixtures thereof in all ratios.

The compounds of the formula II can also be their pharmaceutically usable derivatives, salts, solvates and stereoisomers, including mixtures thereof in all ratios.

Regarding further properties and features and the preparation of representatives of this class of compound, reference is made to WO 2007/093264 A1 of the applicant, the disclosure content of which is incorporated in full into the contents of the present description by way of express reference.

In a preferred embodiment, the compounds of the formula II are selected from N'-[2-hydroxy-2-(3,4-difluorophenyl)acetyl]-4-hydroxy-2-ethyl-3-methylbenzohydrazide and N'-[2-(3,5-difluorophenyl)-2-hydroxyacetyl]-2-ethyl-4-hydroxy-3-methylbenzohydrazide. Preference is given to the last-mentioned compound of the formula I, the preparation of which, as already mentioned, is also described below.

The viral diseases are preferably selected from the group lymphocytic choriomeningitis, viral hepatitis, viral myocarditis, AIDS, herpes, papilloma and viral lung inflammation. For the purposes of the present invention, herpes and papilloma are intended to be taken to mean infections or infectious diseases which are caused by herpes or papilloma viruses.

The carcinomas are preferably selected from the group colon carcinoma, mammacarcinoma, stomach carcinoma and lung carcinoma.

Furthermore, the compounds of the formula II can be in the form of pharmaceutical formulations. Pharmaceutical formulations of this type can be adapted for administration via any desired suitable route, for example by oral, rectal, nasal, topical, vaginal or parenteral routes. Formulations of this type can be prepared with the aid of methods known in the pharmaceutical sector, for example by combining said compounds with the excipient(s) or adjuvant(s).

Regarding further features and details of the possible pharmaceutical formulations of the compounds of the formula II, reference is likewise made to WO 2007/093264 A1.

A therapeutically effective amount of a compound of the present invention depends on a number of factors, including, for example, the age and weight of the person or animal, the precise condition requiring treatment, and its severity, the nature of the formulation and the administration route, and is ultimately determined by the treating doctor or veterinarian. However, an effective amount of a compound according to the invention for the treatment is generally in the range from 0.1 to 1000 mg/kg of body weight of the recipient (mammal) per day, in particular in the range from 0.1 to 100 mg/kg of body weight per day and particularly typically in the range from 1 to 10 mg/kg of body weight per day. Thus, the actual amount per day for an adult mammal weighing 70 kg is usually between 70 and 700 mg, where this amount can be given as a single dose per day or more usually in a series of part-doses (such as, for example, two, three, four, five or six) per day, so that the total daily dose is the same. An effective amount of a salt or solvate or of a physiologically functional derivative thereof can be determined as the proportion of the effective amount of the compound according to the invention per se. It can be assumed that similar doses are suitable for the treatment of the other conditions mentioned above.

The present invention also relates to the use of compounds of the formula II for the preparation of a medicament for the prophylaxis and/or treatment of viral diseases and/or carcinomas. Regarding further features and details, reference is made to the description above.

Finally, the invention also relates to a method for the prophylaxis and/or treatment of viral diseases and/or carcinomas, comprising the administration of a therapeutically effective amount of compounds of the formula II. The expression "therapeutically effective amount" here means an amount of said compounds, or of medicaments or pharmaceuticals based thereon, which, compared with a corresponding patient who has not received this amount, has the following effect: improved therapy, healing, prevention or curing of a disease, syndrome, condition, complaint, disorder or side effects or also the reduction in the progress of a disease, complaint or disorder. Regarding further features and details, reference is likewise made to the description above.

The present invention furthermore also relates to the compounds described in WO 2006/105850 A1 of the applicant and depicted by the formula I for the prophylaxis and/or treatment of viral diseases and/or carcinomas. Regarding further properties and features and the preparation of these compounds, reference is made to WO 2006/105850 A1 of the applicant, the disclosure content of which is incorporated in full into the contents of the present description by way of express reference.

The existing and further features of the invention arise from the following description of preferred embodiments in combination with the sub-claims and the figures. The individual features here may in each case be achieved alone or severally in combination with one another.

EXAMPLES

Figure 1:
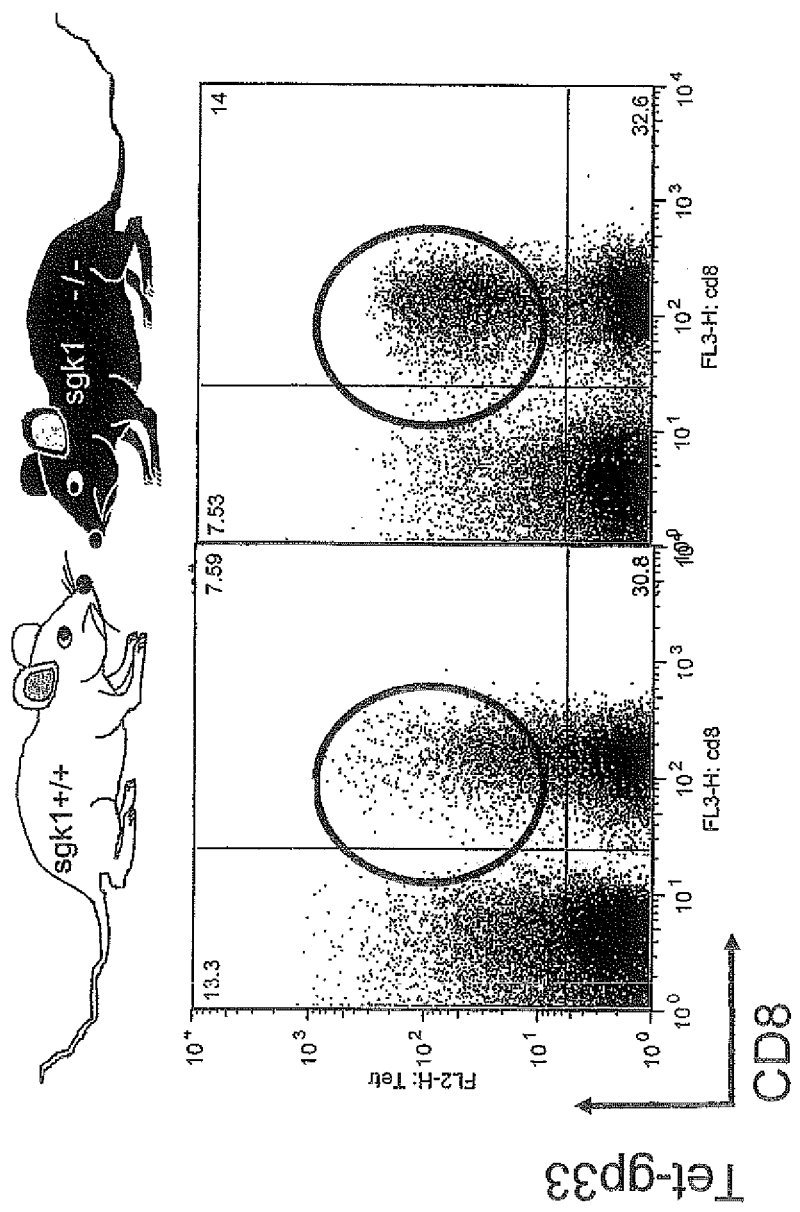
FIG. 1: an increased CD8$^+$ T-cell response to lymphocytic choriomeningitis virus (LCMV) in, SGKI knockout mice.

I. N'-[2-(3,5-Difluorophenyl)-2-hydroxyacetyl]-2-ethyl-4-hydroxy-3-methylbenzohydrazide (EMD 638683)

70.0 g of N'-[2-(3,5-difluorophenyl)-2-hydroxyacetyl]-2-ethyl-4-methoxy-3-methylbenzohydrazide (A1) are suspended in 350 ml of dichloromethane. 105 ml of boron tribromide are then added dropwise. The reaction mixture is stirred at room temperature for 3 hours. The resultant solution is subsequently carefully decanted into one litre of ice-water. The aqueous phase is extracted twice with 500 ml of ethyl acetate. The combined organic phases are then extracted once with 300 ml of water, dried over sodium sulfate and subsequently filtered. The filtrate is concentrated in vacuo. The resultant residue is, then recrystallised from 500 ml of acetonitrile using activated carbon, giving 32.2 g of the title compound as colourless solid having a melting point of 187.4° C. (MS: 365 (MH$^+$), TLC: Rf=0.29 (cyclohexane/methyl tert-butyl ether 1:4, parts by volume).

Ia. N'-[(S)-2-(3,5-Difluorophenyl)-2-hydroxyacetyl]-2-ethyl-4-hydroxy-3-methylbenzohydrazide a) Chromatographic Racemate Separation (No Fig.):

500 mg of Example 1 (EMD 638683) are dissolved in 4 portions in 5 ml of 2-propanol and 5 ml of n-heptane in each case at elevated temperature. The solutions are subsequently chromatographed on 2 serial Chiralpak AD (5×20 cm) chromatography columns (Daicel) with the solvent mixture n-heptane/12-propanol (4:1, parts by volume; 0.8 ml/min) (retention time: 6.11 min). The combined product fractions are evaporated to dryness in vacuo, giving 245 mg of the title compound in analytically and enantiomerically pure form as colourless solid having a melting point of 202.3° C. MS: 365 (M+Fr), 382 (M+NH$_4^+$); TLC: Rf=0.29 (cyclohexane/methyl tert-butyl ether 1:4, parts by volume); $[\alpha]^{20}_D$=+30.4° (c=0.0201 g/2 ml of methanol).

b) From A2:

The title compound is prepared analogously from N'-[(S)-2-(3,5-difluorophenyl)-2-hydroxyacetyl]-4-benzyloxy-2-ethyl-3-methylbenzohydrazide (A2) as described for compound 3.

Ib. N'-[(R)-2-(3,5-Difluorophenyl)-2-hydroxyacetyl]-2-ethyl-4-hydroxy-3-methylbenzohydrazide a) Chromatographic Racemate Separation (No Fig.):

500 mg of Example 1 (EMD 638683) are dissolved in 4 portions in 5 ml of 2-propanol and 5 ml of n-heptane in each case at elevated temperature. The solutions are subsequently chromatographed on 2 serial Chiralpak AD (5×20 cm) chromatography columns (Daicel) with the solvent mixture n-heptane/2-propanol (4:1, parts by volume; 0.8 ml/min) (retention time: 9.36 min). The combined product fractions are evaporated to dryness in vacuo, giving 250 mg of the title compound as colourless solid having a melting point of 203.7° C. MS: 365 (M+H$^+$); TLC: Rf=0.29 (cyclohexane/methyl tert-butyl ether 1:4, parts by volume); $[\alpha]^{20}_D$=−29.7° (c=0.0184 g/2 ml of methanol), enantiomeric excess 98.2%.

b) From A3:

45 mg of N'-[(R)-2-(3,5-difluorophenyl)-2-hydroxyacetyl]-4-benzyloxy-2-ethyl-3-methylbenzohydrazide (A3) are dissolved in 100 ml of methanol. The reaction solution is subsequently hydrogenated in an H-Cube® (ThalesNano) on 10% Pd/C (55×4 mm cartridge) (flow rate: 1 ml/min, mode: full H$_2$, 30° C., atmospheric pressure). The reaction solution is subsequently evaporated to dryness and purified by means of preparative HPLC (Chromolith® prep RP18e 100-25 mm, Merck; solvent gradient: water/1-50% by vol. of acetonitrile), giving 10 mg of the title compound after freeze-drying as amorphous, colourless lyophilisate; MS: 751.2 (2M+Na$^+$); TLC: Rf=0.31 (cyclohexane/methyl tert-butyl ether 1:4, parts by volume), enantiomeric excess>50%.

Intermediate Compounds

A1. N'-[2-(3,5-Difluorophenyl)-2-hydroxyacetyl]-2-ethyl-4-methoxy-3-methylbenzohydrazide 106.0 g of 3,5-difluorophenylhydroxyacetohydrazide (B2) are dissolved in 820 ml of N,N-dimethylformamide. 104.9 g of 2-ethyl-4-methoxy-3-methylbenzoic acid (B1), 153.9 g of N-3-dimethylaminopropyl-N'-ethylcarbodiimide hydrochloride (DAPECI) and 42.8 g of hydroxybenzotriazole (HOBt) are subsequently added. The reaction mixture is cooled in an ice bath during the addition of the compounds enumerated above. The solution is then stirred at room temperature for 24 hours. For work-up, the reaction mixture is diluted with 3.5 litres of water. The resultant suspension is stirred for one hour, subsequently filtered off and washed with additional water. The filter cake is recrystallised from 2.5 litres of methanol, giving 129.0 g of the title compound as colourless solid having a melting point of 197.1° C. (MS: 401 (MNa$^+$)).

A2. N'-[(S)-2-(3,5-Difluorophenyl)-2-hydroxyacetyl]-4-benzyloxy-2-ethyl-3-methylbenzohydrazide The title compound is prepared analogously using (S)-methyloxazaborolidine [(S)-Me-CBS] as described for intermediate A3.

A3. N'-[(R)-2-(3,5-Difluorophenyl)-2-hydroxyacetyl]-4-benzyloxy-2-ethyl-3-methylbenzohydrazide 302 mg of N'-[2-(3,5-difluorophenyl)-2-oxoacetyl]-4-benzyloxy-2-ethyl-3-methylbenzohydrazide (B3) are dissolved in 25 ml of tetrahydrofuran. This solution is added dropwise over the course of 5 min to a solution of 49 μl of borane/dimethyl sulfide complex and 55 μl of (R)-methyloxazaborolidine [(R)-Me-CBS, 1-1.5 M in toluene) in 17 ml of tetrahydrofuran at a temperature of (−)78° C. The cooling bath is subsequently removed, and the solution is stirred for 6 h, during which the reaction solution warms to room temperature: 100 ml of water are then added, and the mixture is extracted three times with 150 ml of ethyl acetate each time. The combined organic phases are washed with 40 ml of each of water, 0.1 M HCl and sat. NaCl solution, dried over NaSO4, filtered off with suction and evaporated to dryness. The residue is purified by means of preparative HPLC (solvent gradient: water/1-50% by vol. of acetonitrile), giving 63 mg of the title compound as colourless, amorphous solid. MS: 932 (2M+Na$^+$); TLC: Rf=0.56 (cyclohexane/methyl tert-butyl ether 1:4, parts by volume).

B1. 2-Ethyl-4-methoxy-3-methylbenzoic acid 20.0 g of 4-methoxy-2,3-dimethylbenzoic acid (C1) are dissolved in one litre of tetrahydrofuran in a dry nitrogen atmosphere and subsequently cooled to −78° C. 300 ml of sec-butyllithium (1.4 M in cyclohexane) are then added dropwise to give a red solution. The red solution is stirred at −78° C. for a further hour. 34.5 ml of methyl iodide are then added, and the resultant suspension is stirred for one hour without cooling. 300 ml of water are subsequently added, and the solution is extracted, using ethyl acetate, twice with 300 ml of ethyl acetate each time. The aqueous phase is subsequently filtered, the filtrate is cooled in an ice bath, adjusted to pH 1 by addition of hydrochloric acid (3.0 M) and stirred for a further 30 minutes. The suspension is then filtered and washed with water. The filter cake is dried at 110° C. in vacuo, giving 20.9 g of the title compound as colourless solid having a melting point of 180° C. (MS: 195.2 (MH$^+$)).

B2. 3,5-Difluorophenylhydroxyacetohydrazide 5.0 g of methyl 3,5-difluorophenylhydroxyacetate (C2) are dissolved in 45.0 ml of 2-propanol. 1.32 ml of hydrazine hydrate are then added dropwise, and the reaction mixture is kept under reflux for 18 hours. The solution is subsequently evaporated to dryness, and the resultant residue is purified by flash chromatography on silica gel (gradient for elution: ethyl acetate/0-20.0% by vol. of methanol), giving 3.70 g of the title compound as colourless solid having a melting point of 119.3° C. (MS: 202.8 (MH$^+$)).

B3. N'-[2-(3,5-Difluorophenyl)-2-oxoacetyl]-4-benzyloxy-2-ethyl-3-methylbenzohydrazide 172 mg of N'-[2-(3,5-difluorophenyl)-2-hydroxyacetyl]-4-benzyloxy-2-ethyl-3-methylbenzohydrazide (C3) are dissolved in 0.9 ml of dimethyl sulfoxide and 28 ml of dichloromethane under a dry nitrogen atmosphere. 185 mg of triacetoxyperiodinane (Dens-Martin reagent) are subsequently added. The suspension is stirred at room temperature for 1 h. For work-up, 100 ml of dichloromethane and 30 ml of 0.5 M Na$_2$S$_2$O$_3$ solution are added. The organic phase is subsequently extracted with 50 ml of sat. NaHCO$_3$ solution, dried over Na$_2$SO$_4$, filtered off with suction and evaporated to dryness. The residue is purified by means of flash column chromatography on silica gel (solvent gradient: cyclohexane/0-30% by vol. of methyl tert-butyl ether), giving 163 mg of the title compound as amorphous solid; MS: 452.7 (2M+H$^+$); TLC: Rf=0.37 (cyclohexane/ethyl acetate 2:1, parts by volume).

C1. 4-Methoxy-2,3-dimethylbenzoic acid 60.0 g of 2,3-dimethyl-4-methoxybenzaldehyde (DI) are dissolved in 1.20 l of dimethyl sulfoxide. A solution of 131.5 g of sodium dihydrogenphosphate and 132.2 g of sodium chlorite in 480 ml of water is subsequently added dropwise, during which the temperature of the reaction batch is kept below 40° C. The reaction mixture is then stirred at room temperature for a further 2 hours. For work-up, the suspension is diluted with 2.0 l of water and stirred for a further hour. The resultant precipitate is filtered, washed with water and dried at 100° C. in vacuo, giving 65.0 g of the title compound as colourless solid having a melting point of 214° C. (MS: 181.2 (MH$^+$)).

C2. Methyl 3,5-difluorophenylhydroxyacetate 25.0 g of 3,5-difluorophenylhydroxyacetic acid (D2) are dissolved in 325 ml of methanol. 3.9 g of boric acid are subsequently added, and the reaction mixture is stirred at room temperature for 18 hours. The resultant solution is then evaporated to dryness. The residue is extracted using 100 ml of ethyl acetate and 100 ml of water. The aqueous phase is subsequently extracted twice with 50 ml of ethyl acetate each time. The combined organic phases are dried over sodium sulfate and filtered. The filtrate is evaporated to dryness in vacuo, giving 25.5 g of the title compound as crude product. Recrystallisation from 17 ml of ethyl acetate and 170 ml of cyclohexane give 23.5 g of the pure compound C2 having a melting point of 61.8° C. (MS 201.9 (M$^+$)).

C3. N'-[2-(3,5-Difluorophenyl)-2-hydroxyacetyl]-4-benzyloxy-2-ethyl-3-methylbenzohydrazide Compound C3 is synthesised analogously to the preparation described for A1 starting from 4-benzyloxy-2-ethyl-3-methylbenzoic acid and intermediate B2.

D1. 2,3-Dimethyl-4-methoxybenzaldehyde

Compound D1 was purchased from ABCR GmbH & Co. KG.

D2. 3,5-Difluorophenylhydroxyacetic acid

Compound D2 was purchased from Sigma-Aldrich Co.

Biochemical Assay

The compounds according to the invention described in the Examples were tested in the assay described below, and it was found that they have a kinase-inhibiting action. Further assays are known from the literature and could easily be carried out by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

The inhibition of SGK1 protein kinase can be determined in the filter binding method.

| Biochemical data | |
|---|---|
| Compound No. | SGK1 enzyme inhibition $IC_{50}$ |
| I | >300 nM |
| Ia | >300 nM |
| Ib | <300 nM |

DESCRIPTION OF THE FIGURES

FIG. 1 shows a dot plot of virus-specific (Tet-9P 33$^+$) CD8$^+$ T lymphocytes in the blood of SGK1 knockout mice (SGK1$^{-/-}$, right-hand dot plot) and their wild-type sibling mice (SGK1$^{+/+}$, left-hand dot plot). To this end, SGK1 knockout mice and wild-type sibling mice were each infected with 2×10$^6$ pfu (plaque forming units) of LCMV (choriomeningitis virus). On day 8 after infection, the blood was stained with the aid of the so-called tetramer technique for virus-specific CD8$^+$ T-cells, and the virus-specific CD8$^+$ T-cells were subsequently identified and quantified with the aid of FACS analysis (fluorescence activated cell sorting, flow cytometry). The dot plots depicted in FIG. 1 document an increased immune defence to LCMV in the SGK1 knockout mice.

Figure 2:
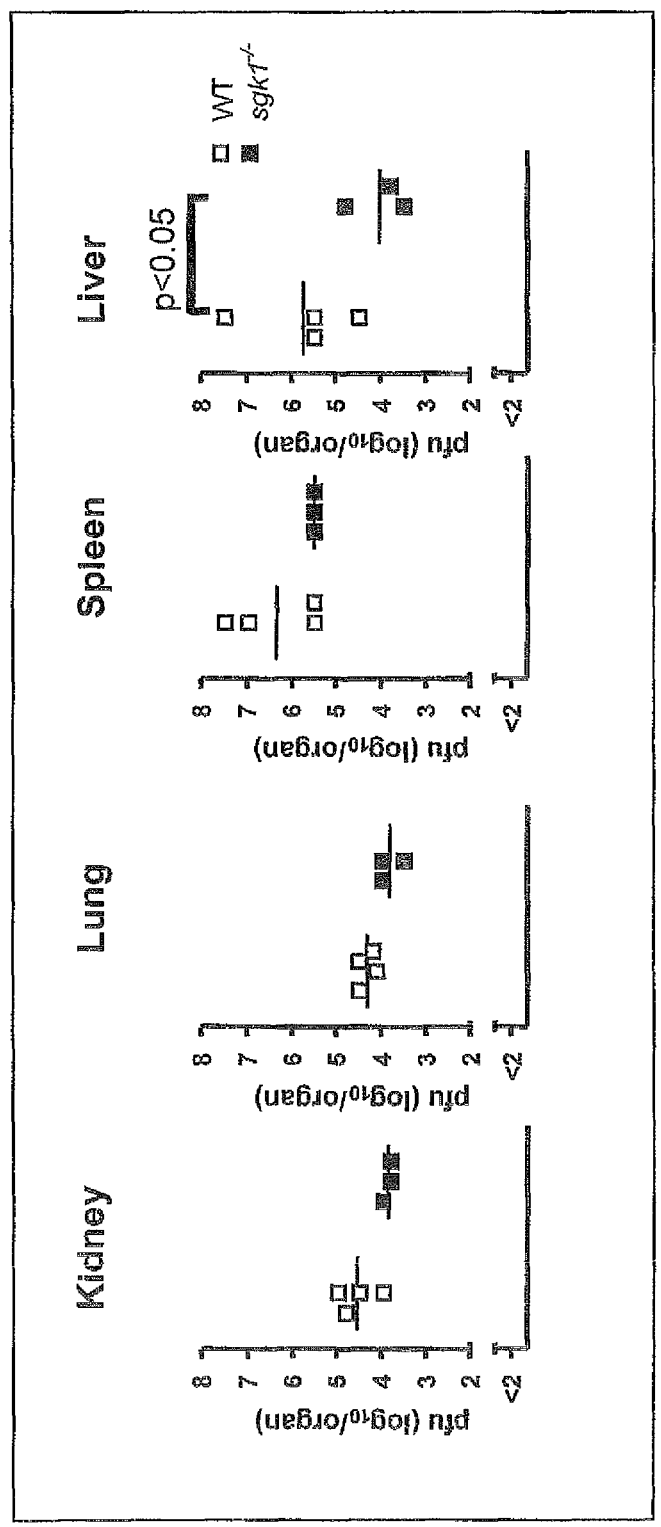
FIG. 2: viral replication of LCMV in various tissues in SGKI knockout mice and SGKI wild-type sibling mice.

FIG. 2 reproduces graphically the number of plaque forming units of LCMV-infected SGK1 knockout mice (SGK1$^{-/-}$, solid squares) and their wild-type sibling mice (WT, open squares) in various tissues. To this end, the SGK1 knockout mice and the wild-type sibling mice were infected with in each case 2×10$^6$ pfu (plaque forming units) of LCMV. On day 8 after infection, the virus titres were analysed with the aid of the so-called plug assay in the various tissues (kidney, lung, spleen and liver tissue). The decimal logarithm of the number of plaque forming units (pfu) is in each case plotted on the ordinates of the graphs depicted in FIG. 2. The graphs reproduced in FIG. 2 show that the number of plaque forming units of LCMV in the various tissue types is smaller in the SGK1 knockout mice than in the wild-type sibling mice.

Figure 3:
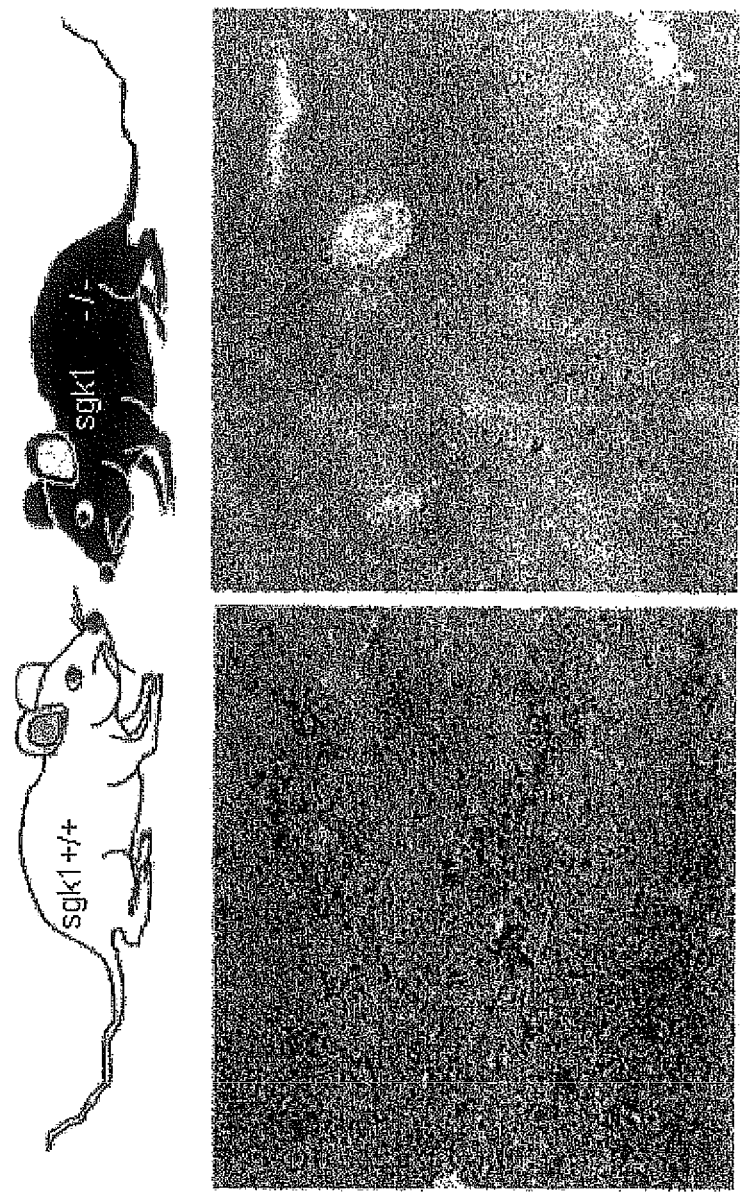
FIG. 3: the result of an immunohistochemical investigation of LCMV antigen in SGK1 knockout mice and wild-type sibling mice.

FIG. 3 shows the result of an immunohistochemical investigation of LCMV antigen in SGK1 knockout mice (SGK1$^{-/-}$, right) and wild-type sibling mice (left). To this end, SGK1 knockout mice and wild-type sibling mice were each infected with 2×10$^6$ pfu of LCMV. On day 8 after infection, liver tissue from SGK1 knockout mice and from wild-type sibling mice was subsequently investigated immunohistochemically for LCMV antigen.

Figure 4:
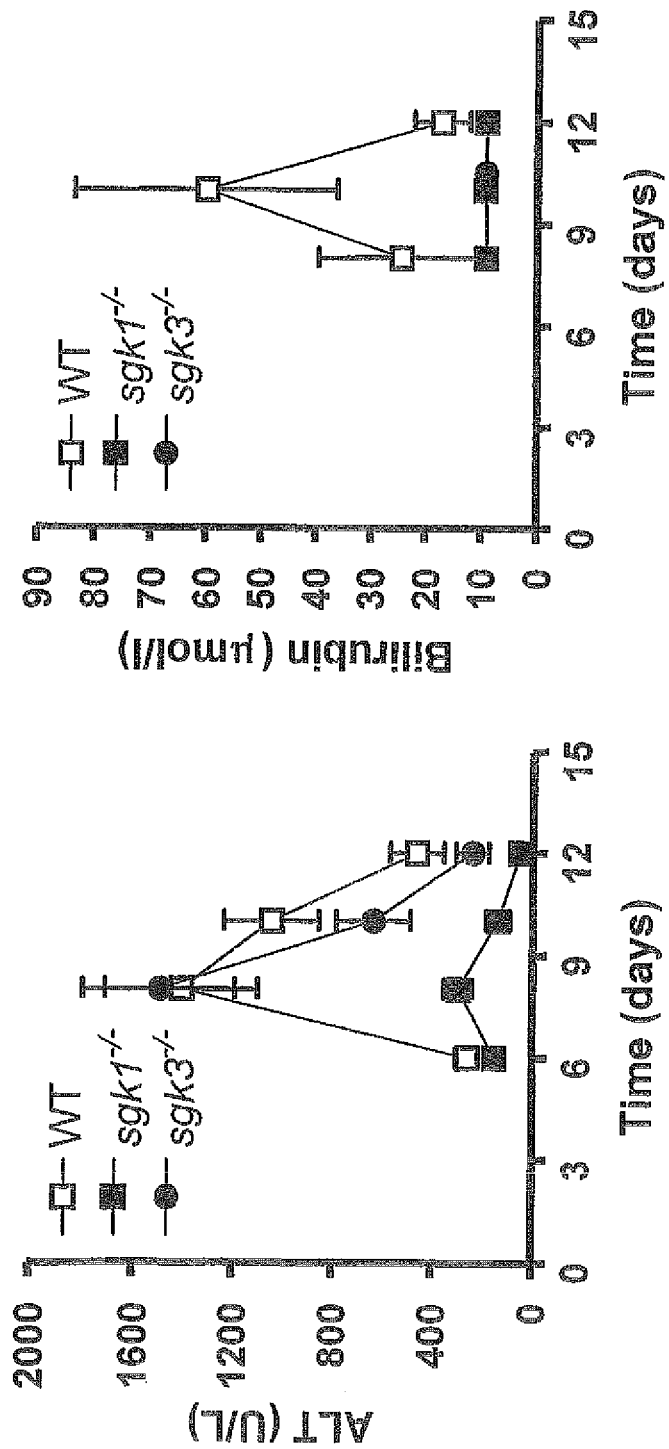
FIG. 4: the influence of SGK1 on the course of viral hepatitis.

FIG. 4 shows the influence of SGK1 on two typical hepatitis markers, namely the liver enzyme alanine aminotransferase (left-hand graph) and bilirubin (right-hand graph). Both markers occur to an increased extent in liver tissue in the case of hepatitis.

The concentration of alanine aminotransferase (ALT), expressed in units per litre of tissue fluid (U/L), is reproduced on the ordinate of the left-hand graph of FIG. 4. The time in days is reproduced on the abscissa. The bilirubin concentration, expressed in µmol per litre of tissue fluid, is plotted on the ordinate of the right-hand graph of FIG. 4. The time, expressed in days, is likewise reproduced on the abscissa.

The graphs depicted in FIG. 4 show that the concentrations of alanine aminotransferase and bilirubin are significantly reduced in LCMV-induced hepatitis in SGK1 knockout mice (SGK1$^{-/-}$, solid squares) compared with the corresponding values in wild-type sibling mice (WT, open squares). These data confirm that "switching-off" or inhibition of SGK1 has a favourable effect on the course of viral hepatitis from therapeutic points of view. The graphs depicted in FIG. 4 additionally show that SGK3 does not have a favourable effect on the course of viral hepatitis (cf. in this respect the solid circles depicted in the graphs of FIG. 4, which reflect the corresponding values of SGK3 knockout mice (SGK3$^{-/-}$)). Overall, the SGK1 knockout mice and the wild-type sibling mice (as well as the SGK3 knockout mice) were each also infected with 2×10$^6$ pfu of LCMV in this case.

Figure 5:
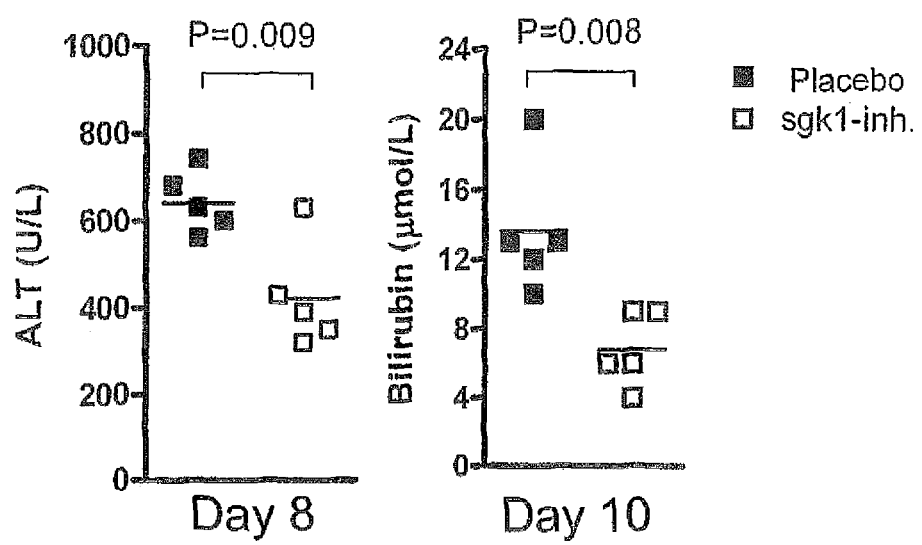
FIG. 5: effect of an SGK1 inhibitor on the course of viral hepatitis.

FIG. 5 shows graphically the influence of the SGK1 inhibitor N'-[2-(3,5-difluorophenyl)-2-hydroxyacetyl]-2-ethyl-4-hydroxy-3-methylbenzohydrazide on the concentration of alanine aminotransferase and bilirubin. SGK1 wild-type mice of type 10 C57BL/6 were fed with placebo feed. After one week, one group of the experimental animals was treated with the SGK1 inhibitor. The SGK1 inhibitor had been added to the feed in a mixing ratio of 4.46 mg/g of feed. This corresponds to an approximate dose of 600 mg/kg of body weight. Only the placebo feed was continued to be administered to the other group. After a further week, the SGK1 knockout mice were each infected with 2×10$^6$ pfu of LCMV in order to induce viral hepatitis in this way. The values for the alanine aminotransferase were measured 8 days after infection and the corresponding values for bilirubin 10 days after infection. The concentration of alanine aminotransferase is reproduced on the ordinate of the left-hand graph of FIG. 5 (U/l, enzyme units per litre of tissue fluid). The time period of 8 days after LCMV infection is shown on the abscissa. The bilirubin concentration (µmol/l) is depicted on the ordinate of the right-hand graph in FIG. 5. The abscissa shows the time period of 10 days after LCMV infection.

The results reproduced in the graphs of FIG. 5 demonstrate that the concentrations of the hepatitis markers alanine aminotransferase and bilirubin are significantly reduced in the experimental animals which were treated with the SGK1 inhibitor before infection (open squares), in contrast to the experimental animals which were not with the SGK1 inhibitor (solid squares). These data confirm that the SGK1 inhibitor has properties which favour the course of viral hepatitis and can thus be employed for the prophylaxis or treatment of viral hepatitis.

Figure 6:
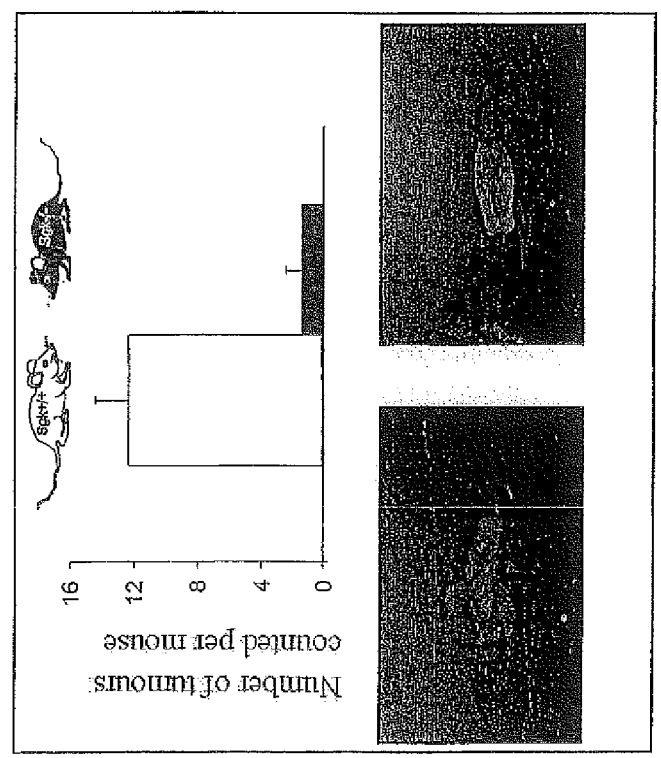
FIG. 6: the development of colon carcinomas in SGK1 knockout mice compared with SGK1 wild-type mice.
Figure 8:
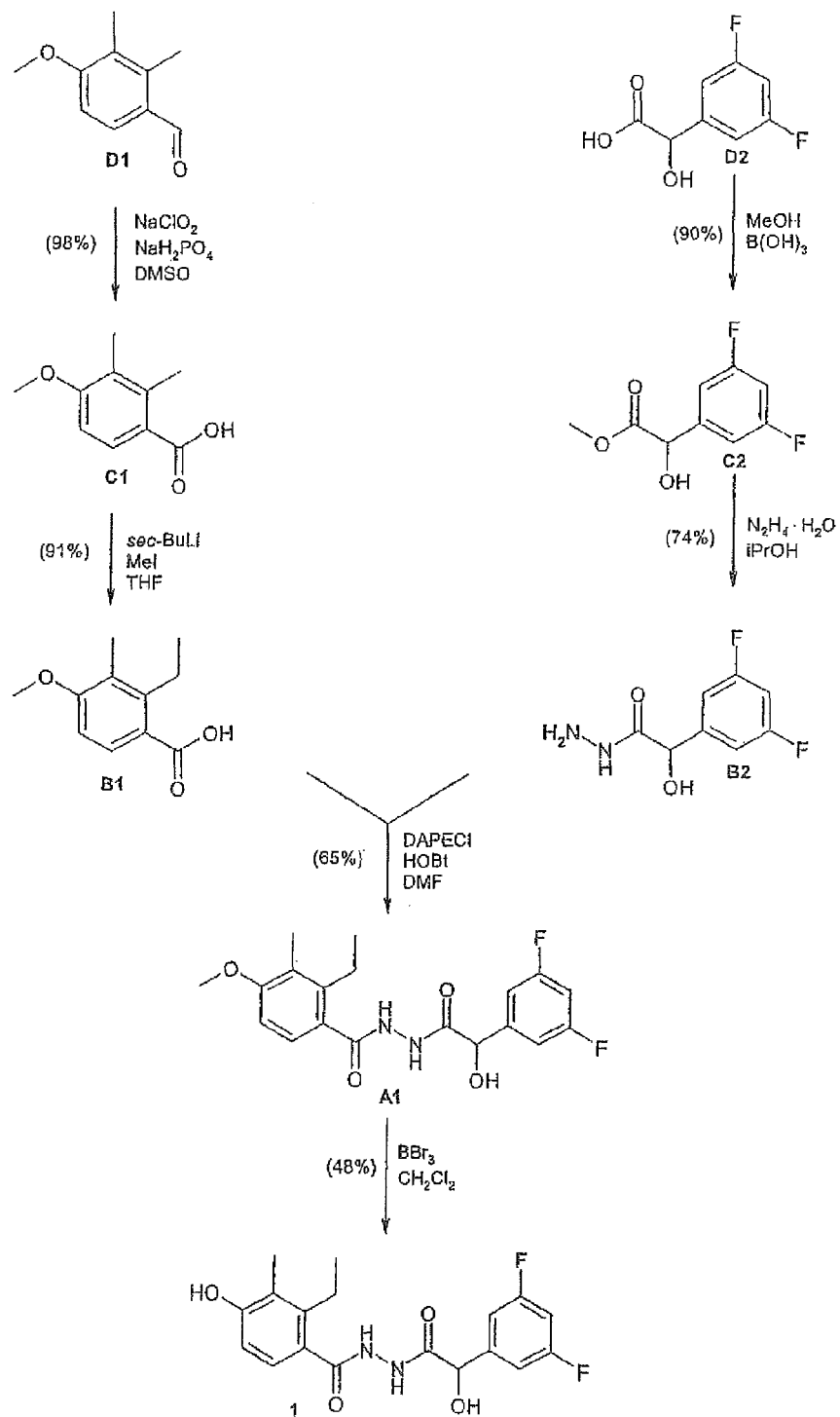
FIG. 8: a synthesis scheme of the SGK1 inhibitor N'-[2-(3,5-difluorophenyl)-2-hydroxyacetyl]-2-ethyl-4-hydroxy-3-methylbenzohydrazide I (EMD 638683)
Figure 9:
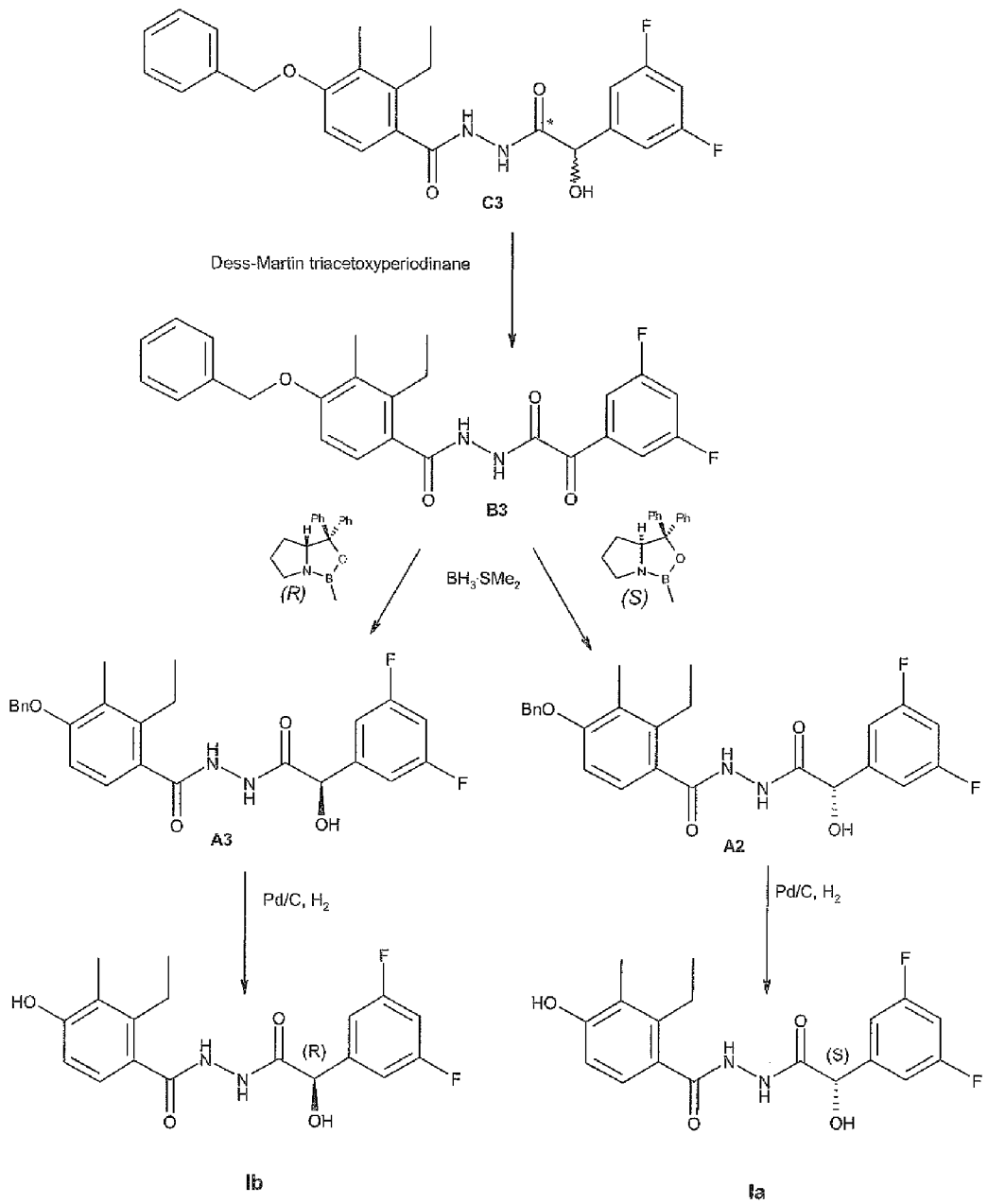
FIG. 9: a synthesis scheme of the enantiomeric SGK1 inhibitors N'-[(S)-2-(3,5-difluorophenyl)-2-hydroxyacetyl]-2-ethyl-4-hydroxy-3-methylbenzohydrazide (Ia) N'-[(R)-2-(3,5-difluorophenyl)-2-hydroxyacetyl]-2-ethyl-4-hydroxy-3-methylbenzohydrazide (Ib)

FIG. 6 shows the development of colon carcinomas in SGK1 knockout mice (SGK1$^{-/-}$ mice) compared with SGK1 wild-type mice (SGK$^{+/+}$ mice). To this end, colon tumours were induced chemically in the experimental animals (Wang J G, Wang D F, Lv B J, Si J M: A novel mouse model for colitis-associated colon carcinogenesis induced by 1,2-dimethylhydrazine and dextran sulfate sodium. World J Gastroenterol 2004; 10:2958-2962). Some of the experimental animals were subjected to three cycles of chemical tumour genesis at an age of 8 weeks. To this end, the animals were treated intraperitoneally with 20 mg/kg of 1,2-dimethylhydrazine (DMH; Sigma-Aldrich Corporation. St. Louis. Mo. USA). Starting one week later, distilled water containing 30 g/l of synthetic dextran sulfate sodium (DSS; molecular weight 5000; Wako Pure Chemical Industries Ltd. Japan) was administered to the animals three times for 7 days and distilled water was administered for a further 14 days (total duration 3×(1+2 weeks)=9 weeks in total). The remainder of the experimental animals (control animals) were instead supplied intraperitoneally by injection with 20 mg/kg of a 0.9% sodium chloride solution. All mice were anaesthetised with ether at the age of 22 weeks and subsequently killed.

The result of chemically induced tumour genesis shown graphically in FIG. 6 clearly shows that the sensitivity of SGK1 knockout mice (reproduced by the solid bars on the right) to chemically induced colon tumours is significantly reduced, in contrast to SGK1 wild-type mice (reproduced by the open bars on the left). This result is all the more surprising as the specialist literature reports downregulation of SGK1 in carcinomatous tissue regarding various types of carcinoma (Rauhala H E, Porkka K P, Tolonen T T, Martikainen P M, Tammela T L, Visakorpi T: Dual specificity phosphatase 1 and serum/glucocorticoid-regulated kinase are downregulated in prostate cancer. Int J Cancer 2005; Chu S, Rushdi S, Zumpe E T, Mamers P, Healy D L; Jobling T, Burger H G, Fuller P J: FSH-regulated gene expression profiles in ovarian tumours and normal ovaries. Mol Hum Reprod 2002; 8:426-433; Chung E J, Sung Y K, Farooq M, Kim Y, Im S, Tak W Y, Hwang Y J, Kim Y I, Han H S, Kim J C, Kim M K: Gene expression profile analysis in human hepatocellular carcinoma by cDNA microarray. Mol Cells 2002; 14:382-387), which is why it would actually have been expected that inhibition of SGK1 promotes tumour growth.

Figure 7:
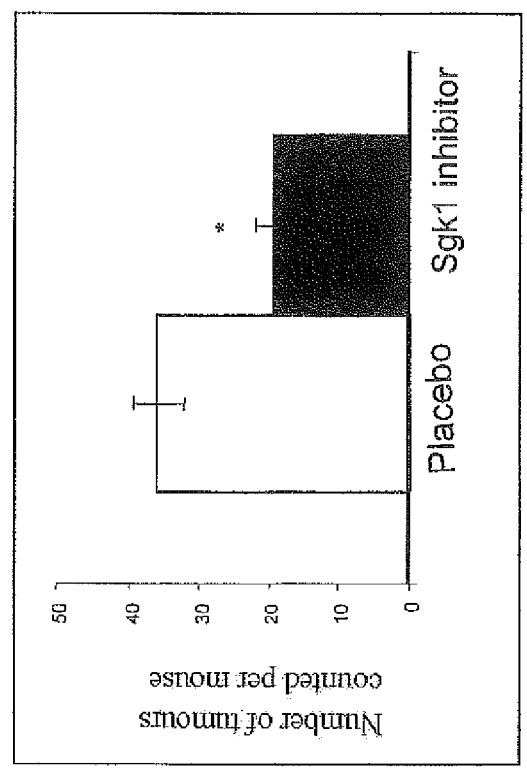
FIG. 7: the inhibition of colon carcinomas by an SGK1 inhibitor.

FIG. 7 shows graphically the effect of the SGK1 inhibitor N'-[2-(3,5-difluorophenyl)-2-hydroxyacetyl]-2-ethyl-4-hydroxy-3-methylbenzohydrazide on the formation of colon carcinomas. Firstly, chemically induced tumour genesis was carried out as described in the figure description for FIG. 6. One week after the treatment, either a placebo or the SGK1 inhibitor was administered for 20 days. The SGK1 inhibitor had been added to the feed in a mixing ratio of 4.46 mg/g of feed. This corresponds to an approximate dose of 600 mg/kg of body weight. The graph shown in FIG. 7 makes it clear that, in the case of the experimental animals treated with the SGK1 inhibitor, the growth of colon tumours (solid bars on the right) is significantly inhibited compared with the untreated experimental animals (open bars on the left).

We claim:

1. A compound of formula Ia or Ib:

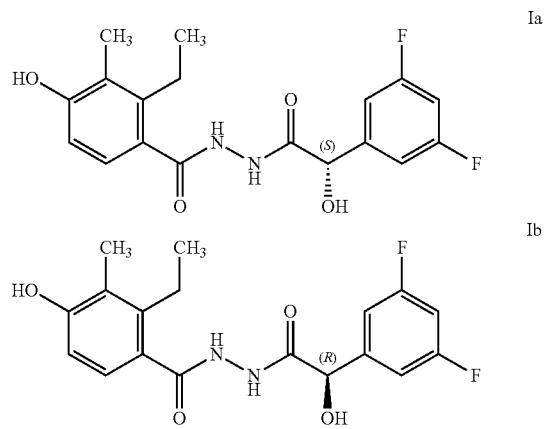

or a pharmaceutically acceptable tautomer, salt, stereoisomer or enantiomer thereof or a mixture thereof in all ratios.

2. A method for the treatment of a viral disease which is lymphocytic choriomeningitis (LCM), viral hepatitis, viral myocarditis, AIDS, herpes, papilloma, or viral lung inflammation, comprising administering to a host in need thereof a compound of formula Ia or Ib according to claim 1.

3. A method for the treatment of a carcinoma which is colon carcinoma, mammacarcinoma, stomach carcinoma or lung carcinoma, comprising administering to a host in need thereof a compound of formula Ia or Ib according to claim 1.

4. A pharmaceutical composition comprising at least one compound of Formula Ia or Ib according to claim 1 and a pharmaceutically acceptable excipient or adjuvant.

5. A method for the treatment of a viral disease which is lymphocytic choriomeningitis (LCM), viral hepatitis, viral myocarditis, AIDS, herpes, papilloma, or viral lung inflammation, comprising administering to a host in need thereof the pharmaceutical composition according to claim 4.

6. A method for the treatment of a carcinoma which is colon carcinoma, mammacarcinoma, stomach carcinoma or lung carcinoma, comprising administering to a host in need thereof the pharmaceutical composition according to claim 4.

* * * * *

UNITED STATES PATENT AND TRADEMARK OFFICE
CERTIFICATE OF CORRECTION

PATENT NO. : 8,546,613 B2  Page 1 of 1
APPLICATION NO. : 12/867963
DATED : October 1, 2013
INVENTOR(S) : Thomas Fuchss et al.

It is certified that error appears in the above-identified patent and that said Letters Patent is hereby corrected as shown below:

Title Page, (57) Abstract - Compound II reads:

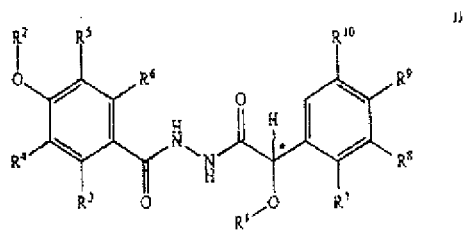

should read:

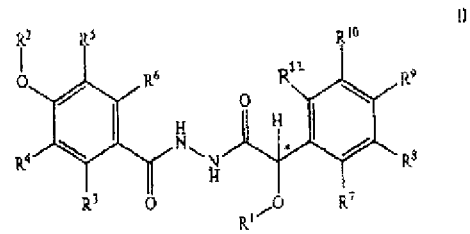

Signed and Sealed this
Thirty-first Day of December, 2013

Margaret A. Focarino
*Commissioner for Patents of the United States Patent and Trademark Office*